US007247315B2

(12) United States Patent
Brown et al.

(10) Patent No.: US 7,247,315 B2
(45) Date of Patent: Jul. 24, 2007

(54) COMPOSITIONS AND MEDICAL DEVICE FOR TRANSDERMAL DELIVERY OF A DRUG AND METHODS OF MAKING AND USING SAME

(75) Inventors: Teletha A. Brown, Piscataway, NJ (US); James Osborne, Princeton Junction, NJ (US); Michael Rudella, Cedar Knolls, NJ (US); Brian Hunt, Harriman, NY (US); Vinod Malik, Toms River, NJ (US)

(73) Assignee: Lavipharm Laboratories Inc., East Windsor, NJ (US)

( * ) Notice: Subject to any disclaimer, the term of this patent is extended or adjusted under 35 U.S.C. 154(b) by 27 days.

(21) Appl. No.: 10/222,007

(22) Filed: Aug. 15, 2002

(65) Prior Publication Data

US 2003/0060479 A1    Mar. 27, 2003

Related U.S. Application Data

(60) Provisional application No. 60/313,055, filed on Aug. 17, 2001.

(51) Int. Cl.
*A61F 13/02* (2006.01)
*A61L 15/16* (2006.01)
*A61K 9/14* (2006.01)

(52) U.S. Cl. .................. 424/448; 424/449; 424/484
(58) Field of Classification Search ............... 424/448, 424/484–489, 449
See application file for complete search history.

(56) References Cited

U.S. PATENT DOCUMENTS

| 4,588,580 | A | * | 5/1986 | Gale et al. ............... 424/449 |
| 4,655,767 | A | * | 4/1987 | Woodard et al. .......... 424/448 |
| 4,806,341 | A | * | 2/1989 | Chien et al. ............... 424/448 |
| 4,814,184 | A | | 3/1989 | Aguadisch et al. |
| 4,906,463 | A | | 3/1990 | Cleary et al. |
| 4,938,759 | A | | 7/1990 | Enscore et al. |
| 5,006,342 | A | | 4/1991 | Cleary et al. |
| 5,064,654 | A | | 11/1991 | Berner et al. |
| 5,186,939 | A | | 2/1993 | Cleary et al. |
| 5,232,702 | A | * | 8/1993 | Pfister et al. ............... 424/448 |
| 5,310,559 | A | | 5/1994 | Shah et al. |
| 5,352,457 | A | | 10/1994 | Jenkins |
| 5,820,875 | A | | 10/1998 | Fallon et al. |
| 6,019,997 | A | | 2/2000 | Scholz et al. |
| 6,139,866 | A | | 10/2000 | Chono et al. |
| 6,231,885 | B1 | | 5/2001 | Carrara |
| 6,235,306 | B1 | | 5/2001 | Miranda et al. |
| 6,730,318 | B2 | * | 5/2004 | Quan et al. ............... 424/448 |
| 2004/0086551 | A1 | | 5/2004 | Miller et al. |

FOREIGN PATENT DOCUMENTS

JP          61134322 A   *   6/1986
WO       WO 89/10108       11/1989

OTHER PUBLICATIONS

PCT International Search Report, Dec. 13, 2002, PCT Search Report.

(Continued)

*Primary Examiner*—Isis Ghali
(74) *Attorney, Agent, or Firm*—Lucas & Mercanti, LLP

(57) ABSTRACT

The invention relates to transdermal delivery patches comprising a drug-containing drug reservoir wherein the drug reservoir comprises a plasticizer composition selected to adjust the rate of drug flux out of the transdermal delivery patch device. The invention also specifically relates to methods of producing the transdermal delivery patches of the invention, the methods comprising the use of an alcohol drug dispersing agent. The invention further specifically relates to methods of treating acute and chronic pain and methods of inducing and maintaining analgesia with the transdermal delivery patches of the invention.

21 Claims, 8 Drawing Sheets

OTHER PUBLICATIONS

Samir D. Roy, et al., Controlled Transdermal Delivery of Fentanyl: . . . , Journal of Pharmaceutical Sciences, vol. 85, No. 5, pp. 491-495, 1996.
Dow Corning 360 Medical Fluid "Online" XP002360693, 2002.
Nair Bindu, et al., Final Report on the Safety Assessment of Stearoxy . . . , International Journal of Toxicology, vol. 22, pp. 11-35, 2003.
Dow Corning: Dow Corning MDX4-4159, 50% Medical Grade Dispersion, pp. 1-5, XP002375283, 2002.

* cited by examiner

COMPOSITIONS AND MEDICAL DEVICE FOR TRANSDERMAL DELIVERY OF A DRUG AND METHODS OF MAKING AND USING SAME

This Application claims benefit to U.S. Provisional Application No. 60/313,055, filed on Aug. 17, 2001, the disclosure of which is incorporated herein by reference in its entirety as if fully set forth herein.

The present invention relates to medical devices comprising a solid drug reservoir formulation for percutaneous administration of a drug, to methods of treating medical conditions with the same, and to methods of preparing such devices. More specifically, the invention relates to transdermal delivery patches comprising a drug reservoir; wherein the drug reservoir comprises a plasticizer composition selected to adjust the rate of flux of the drug out of the transdermal delivery patch device and wherein the drug is selected from the group consisting of fentanyl, oxymorphone, oxycodone, hydromorphone, morphine, buprenorphine and analgesically effective derivatives thereof, preferably fentanyl. The invention also specifically relates to methods of producing the transdermal delivery patches of the invention, the methods comprising the use of an alcohol drug dispersing agent to disperse the drug in a preparative solution. The invention further specifically relates to methods of treating acute and chronic pain and methods of inducing and maintaining analgesia with the transdermal delivery patches of the invention.

Fentanyl and its analgesically effective derivatives (hereafter referred to as "derivatives") such as sufentanyl, carfentanyl, lofentanyl and alfentanyl have long been known as anesthetics and analgesics. Fentanyl and its derivatives are potent, rapidly metabolized drugs having a relatively narrow therapeutic index which produce extremely undesirable side effects on overdosage, most notably respiratory depression. Fentanyl-containing compositions are also relatively expensive and have a high potential for abuse. Skin is known to contain fentanyl binding sites that must be saturated before any significant absorption into the bloodstream occurs. Accordingly, when fentanyl is administered transdermally, the rate of administration to an area of a subject's skin should be controlled in a reproducible fashion to produce an initial dose of fentanyl that rapidly saturates fentanyl skin binding sites, and then provide a more steady medically appropriate flux of fentanyl through an area of skin throughout an administration period. Preferred administration periods for fentanyl patch transdermal delivery devices are about 1-7 days. Thus, medical devices for transdermal administration of fentanyl should provide for a rate-controlled release of fentanyl according to a medically appropriate dose rate during an administration period.

Medical patches for the transdermal delivery of fentanyl, such as those described in U.S. Pat. No. 4,588,580 to Gale et al., often comprise a liquid or semi-solid gel drug reservoir layer that can be made from a variety of compositions, including ethanol based, polyisobutylene/mineral oil based, or silicone adhesive based matrix materials. Liquid or gel based reservoir layers add an additional hazard of drug leakage if the patch is torn. Furthermore, liquid or gel based reservoir layers also have the disadvantage of having to be sealed to ensure against leaking. Sealing of the drug reservoir layer adds to production costs by necessitating one or more additional industrial processing steps. These disadvantages can be avoided using the solid drug reservoir compositions taught in the present invention.

The rate of fentanyl delivery from a medical device for transdermal administration can be regulated in a variety of ways. U.S. Pat. No. 4,938,759 to Enscore et al. discloses a patch for the transdermal delivery of fentanyl wherein the rate of drug delivery is controlled by a combination of dissimilar reservoir and adhesive layer compositions, such as the use of a drug reservoir comprising silicone and polyethylene-(vinyl acetate) copolymer with an adhesive layer comprising polyisobutylene and mineral oil. However, the use of dissimilar materials in transdermal patch layers can compromise the structural integrity or adhesive properties of the transdermal patch device or add to production expenses by necessitating the use of additional materials. U.S. Pat. No. 5,310,559 to Shah et al. provides a rate controlling membrane comprising an acrylate containing polymer for lowering the rate of controlled transdermal release of fentanyl from a medical device. U.S. Pat. No. 6,231,885 teaches the addition of two or more fatty acids or alcohols of different chain lengths to a liquid drug reservoir adhesive layer in order to control the rate of transdermal fentanyl delivery. U.S. Pat. No. 5,820,875 to Fallon et al. discloses a patch that provides a controlled initial pulse of fentanyl followed by a sustained release of fentanyl at a lower level, by employing a combination of a volatile and nonvaolatile solvents in a liquid drug reservoir layer. There remains a need to control the flux rate of a drug from a solid drug reservoir composition without compromising the structural integrity of the medical device.

A prolonged action patch formulation containing fentanyl base is commercially available under the trade name $D_{uragesic}$® from Janssen Pharmaceutica, Titusville, N.J. 08560. The $D_{uragesic}$® patch is a rectangular transparent medical device patch unit comprising a protective liner and four functional layers. Proceeding from the outer surface toward the surface adhesive to skin, the layers of the $D_{uragesic}$® patch are: (1) a backing layer of polyester film, (2) a drug layer of fentanyl and alcohol USP gelled with hydroxyethyl cellulose, (3) a polyethylene (vinyl acetate) copolymer membrane that controls the rate of fentanyl delivery to the skin surface, and (4) a fentanyl containing silicone adhesive. Before use, a protective liner covering the adhesive layer is removed and discarded. However, this product can have the disadvantage of being irritative to administered regions and more expensive to produce than the instant invention. Accordingly, U.S. Pat. No. 6,139,866 discloses a fentanyl transdermal patch formulation comprising certain amounts of fentanyl and sodium acetate as a possible alternative to the $D_{uragesic}$® patch formulation. Still, there remains a need for more affordable medical devices comprising a solid drug reservoir, that offer control of the flux rate of a drug from a drug reservoir composition in a medical device for the transdermal delivery of the drug.

Applicant has discovered that the rate of analgesically effective drugs from a medical device comprising a drug reservoir can be controlled by the addition of certain plasticizers to the drug reservoir and adhesive matrix material. Applicant has also discovered methods of treating chronic and acute pain and methods of providing and maintaining analgesia that utilize the medical devices of the present invention. Accordingly, the present invention avoids numerous shortcomings of prior art patches, such as the potential for undesirable side effects of overdosage, the potential for additional production costs and hazard of drug leakage associated with liquid or gel-based drug reservoirs and the potentially decreased structural integrity of patches comprising layers of dissimilar materials.

In another aspect, the present invention relates to methods of producing the transdermal delivery patches that provide for improved uniformity of mixing of the drug in a reservoir matrix. Prior to the invention, agitation of a solution of the matrix material and the drug was primarily used to uniformly mix the drug in the matrix material. For example, U.S. Pat. No. 6,235,306 to Miranda et al. provides for agitation of a drug composition in a solubilized polydimethylsiloxane matrix material to achieve uniform drug mixing, followed by another step of adding an isopropanol skin permeation enhancer. Applicant has discovered that, during the process of making certain drug containing reservoirs, dispersing the drug composition in an alcohol dispersing agent prior to adding this drug/alcohol dispersing agent mixture to a suitable reservoir layer matrix material surprisingly achieves greater uniformity of the drug in the matrix material used in forming the solid drug reservoir than agitation of the drug and matrix material without the alcohol dispersing agent. Preferably, the alcohol dispersing agent is removed during processing and is substantially absent in the final transdermal patch product. Improving the uniformity of drug dispersion in the drug reservoir layer matrix material is desirable, for example, for providing a more predictable and uniform flux rate of the drug with time and a more spacially uniform drug flux rate across the surface area of the patch.

SUMMARY OF THE INVENTION

In some embodiments, the present invention provides a composition suitable for use in a medical device for transdermal administration of a drug through an area of human skin, the composition comprising a polydimethylsiloxane matrix material and a drug flux rate lowering effective amount of a polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl; wherein the polydimethylsiloxane plasticizer is dimethicone with a viscocity of 20 to 12,500 centistoke; wherein the drug flux rate lowering effective amount of the polydimethylsiloxane plasticizer is between 4 and 7% w/w of the composition; and wherein the polydimethylsiloxane matrix material has a molecular weight of between 100,000 and 5,000,000. In some embodiments, the compositions of the invention comprise no less than 5% w/w and no more than 6% w/w of the polydimethylsiloxane plasticizer, wherein the polydimethylsiloxane plasticizer has a viscosity of 300 to 400 centistoke. In some embodiments, the composition further comprises at least 1.00 mg of drug; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. The composition can, for example, further comprise at least 4% w/w of drug and no more than 6% w/w drug; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl.

In some embodiments, the present invention provides a medical device for transdermal administration of a drug through an area of human skin during an administration period, the medical device comprising a solid drug reservoir, wherein the solid drug reservoir comprises: a flux rate lowering effective amount of a polydimethylsiloxane plasticizer, a pain treating effective amount of a drug and a polydimethylsiloxane matrix material; wherein the polydimethylsiloxane plasticizer is dimethicone with a viscosity of 20 to 12,500 centistoke; wherein the drug flux rate lowering effective amount of the polydimethylsiloxane plasticizer is between 4 and 7% w/w of the solid drug reservoir layer; wherein the polydimethylsiloxane matrix material has a molecular weight of between 100,000 and 5,000,0000; and wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments, the pain treating effective amount of the drug is at least 1 mg of drug in the solid drug reservoir, wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. The medical device can also comprise a backing layer having a top side and a bottom side, wherein the solid drug reservoir layer has a top side and a bottom side and an external edge; the bottom side of the backing layer is contiguously disposed to the top side of the solid drug reservoir layer; and the external edge of the solid drug reservoir layer is not completely sealed by the backing layer.

In some embodiments, the present invention provides a medical device wherein the solid drug reservoir layer has a top side and a bottom side, and wherein: at least 2% w/w of the solid drug reservoir layer is drug and no more than 15% w/w of the solid drug reservoir layer is drug; at least 70% w/w of the solid drug reservoir layer is polydimethylsiloxane matrix material; and at least 5% w/w of the solid drug reservoir is polydimethylsiloxane plasticizer and no more than 6% of the solid drug reservoir is polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments, the medical device further comprises:a backing layer having a top and a bottom side, wherein the bottom side of the backing layer is contiguously disposed with respect to the top side of the solid drug reservoir layer; and a rate controlling membrane having a top and a bottom side; wherein the top side of the rate controlling membrane is contiguously disposed with respect to the bottom side of the drug reservoir layer; wherein the rate controlling membrane can comprise: one or more compositions selected from the group consisting of: low density polyethylene, polyethylene-vinyl acetate copolymer, heat sealable polyester and elastomeric polyester block copolymer; a polyethylene-(vinyl acetate) copolymer with up to 33% vinyl acetate, the copolymer having a molecular weight of 10,000 or greater; the thickness and vinyl acetate composition of the rate controlling membrane are selected to provide a 0.5 to 10 µm/cm²hr permeation rate through the rate controlling membrane at 32 degrees C.; and an adhesive layer having a top and a bottom side; wherein the top side of the adhesive layer is contiguously disposed with respect to the bottom side of the rate controlling membrane; wherein the adhesive layer is adapted to be maintained in drug-transferring relationship to the human skin; wherein: at least 5% w/w and no more than 6% w/w of the adhesive layer is polydimethylsiloxane plasticizer, wherein the polydimethylsiloxane plasticizer is dimethicone with a viscocity of 300-400 centistoke; at least 70% w/w of the adhesive layer is polydimethylsiloxane matrix material, wherein the polydimethylsiloxane matrix material has a molecular weight of between 500,000 to 1,500,000. In some embodiments, the invention provides a medical device wherein: at least 4.5% w/w of the solid drug reservoir layer is drug and no more than 5.5% w/w of the solid drug reservoir layer is drug; at least 5% w/w of the solid drug reservoir layer is polydimethylsiloxane plasticizer and no more than 6% w/w of the solid drug reservoir layer is polydimethylsiloxane plasticizer; and at least 5% w/w of the adhesive layer is polydimethylsiloxane plasticizer; and no more than 6% w/w of the adhesive layer is polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments, the invention provides a medical device of claim 5, wherein: the solid drug reservoir layer is a drug reservoir adhesive layer having a top side and a bottom side, and wherein the solid drug reservoir adhesive layer comprises: at least 2% w/w of the solid drug reservoir adhesive layer is drug and no more than 15% w/w of the solid drug reservoir layer is drug; at least 70% w/w of the solid drug reservoir layer is polydimethylsiloxane matrix material; and at least 5% w/w of the solid drug reservoir is polydimethylsiloxane plasticizer and no more than 6% w/w of the solid drug reservoir is polydimethylsiloxane plasticizer; wherein the drug reservoir adhesive layer is adapted to be maintained in drug-transferring relationship to the human skin; wherein the medical device further comprises a backing layer having a top and a bottom side, wherein the bottom side of the backing layer is contiguously disposed to the top side of the solid drug reservoir adhesive layer; and wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl.

In some embodiments, the invention provides a process for making a solid drug reservoir layer for a medical device for transdermal administration of drug through an area of human skin during an administration period, the process comprising the steps of: dispersing the drug in an initial amount of the drug in an alcohol dispersing agent to form a drug-alcohol dispersion comprising 10 to 50% w/w drug dissolved in the alcohol dispersing agent, wherein the drug-alcohol dispersion does not contain polydimethylsiloxane; and then combining the drug-alcohol dispersion with a polydimethylsiloxane matrix material; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments of the process for making a solid drug reservoir layer for a medical device for transdermal administration of drug, the drug-alcohol dispersion comprises 30 to 50% w/w drug dispersed in the alcohol dispersing agent; and further comprising the steps of admixing the dispersion in a polydimethylsiloxane matrix material in a solution also containing a drug flux rate lowering effective amount of a low molecular weight polydimethylsiloxane plasticizer and casting the resulting mixture as a film and applying heat to reduce the amount of all solvents, including the alcohol dispersing agent, to less than 100 ppm in the medical device; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments, the alcohol dispersing agent is isopropyl alcohol.

In some embodiments, the present invention provides a method of treating acute and chronic pain by transdermally administering a drug, the method comprising the step of: applying and maintaining a medical device for transdermal administration of a drug in drug flow permitting contact with an area of human skin during an administration period; wherein the medical device comprises a solid drug reservoir, wherein the solid drug reservoir comprises: a flux rate lowering effective amount of a polydimethylsiloxane plasticizer, a pain treating effective amount of a drug and a polydimethylsiloxane matrix material; wherein the polydimethylsiloxane plasticizer is dimethicone with a viscocity of 20 to 12,500 centistoke; wherein the drug flux rate lowering effective amount of the polydimethylsiloxane plasticizer is between 4 and 7% w/w of the composition; wherein the polydimethylsiloxane matrix material has a molecular weight of 100,000 to 5,000,000; wherein the pain treating effective amount of the drug is at least 1 mg of fentanyl in the solid drug reservoir; and wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments, the method further comprises a backing layer having a top side and a bottom side, wherein the solid drug reservoir layer has a top side and a bottom side and an external edge; the bottom side of the backing layer is contiguously disposed to the top side of the solid drug reservoir layer; and the external edge of the solid drug reservoir layer is not completely sealed by the backing layer. In some methods of the invention, the solid drug reservoir layer has a top side and a bottom side, and at least 2% w/w of the solid drug reservoir layer is drug and no more than 15% w/w of the solid drug reservoir layer is drug; at least 70% w/w of the solid drug reservoir layer is polydimethylsiloxane matrix material; and at least 5% w/w of the solid drug reservoir is polydimethylsiloxane plasticizer and no more than 6% w/w of the solid drug reservoir is polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some methods of the invention, the medical device further comprises: a backing layer having a top and a bottom side, wherein the bottom side of the backing layer is contiguously disposed with respect to the top side of the solid drug reservoir layer; and a rate controlling membrane having a top and a bottom side; wherein the top side of the rate controlling membrane is contiguously disposed with respect to the bottom side of the drug reservoir layer; wherein the rate controlling membrane comprises: one or more compositions selected from the group consisting of: low density polyethylene, polyethylene-(vinyl acetate) copolymer, heat sealable polyester and elastomeric polyester block copolymer; a polyethylene-(vinyl acetate) copolymer with up to 33% vinyl acetate, the copolymer having a molecular weight of 10,000 or greater, the thickness and vinyl acetate composition of the rate controlling membrane are selected to provide a 0.5 to 10 $\mu m/cm^2 hr$ permeation rate through the rate controlling membrane at 32 degrees C.; and an adhesive layer having a top and a bottom side; wherein the top side of the adhesive layer is contiguously disposed with respect to the bottom side of the rate controlling membrane; wherein the adhesive layer is adapted to be maintained in drug-transferring relationship to the human skin; wherein: at least 5% and no more than 6% w/w of the adhesive layer is polydimethylsiloxane plasticizer, wherein the polydimethylsiloxane plasticizer has a viscosity of 300 to 400 centistoke; at least 70% w/w of the adhesive layer is polydimethylsiloxane matrix material, wherein the polydimethylsiloxane matrix material has a molecular weight of 500,000 to 1,500,000. In some embodiments, at least 4.5% w/w of the solid drug reservoir layer is drug and no more than 5.0% w/w of the solid drug reservoir layer is drug; at least 5% w/w of the solid drug reservoir layer is polydimethylsiloxane plasticizer and no more than 6% w/w of the solid drug reservoir layer is polydimethylsiloxane plasticizer; at least 5% w/w of the adhesive layer is polydimethylsiloxane plasticizer; and no more than 6% w/w of the adhesive layer is polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl.

In some embodiments, the invention provides methods of inducing and maintaining analgesia by transdermally administering a drug, the method comprising the step of: applying and maintaining a medical device for transdermal administration of a drug in drug flow permitting contact with an area of human skin during an administration period; wherein the medical device comprises a solid drug reservoir, wherein the solid drug reservoir comprises: a flux rate lowering effective amount of a polydimethylsiloxane plasticizer, a pain treating effective amount of a drug and a polydimethylsiloxane matrix material; and wherein the polydimethylsiloxane plasticizer is dimethicone with a viscocity of 20 to 12,500 centistoke; wherein the drug flux rate lowering effective amount of the polydimethylsiloxane plasticizer is between 4 and 7% w/w of the composition; wherein the polydimethylsiloxane matrix material has a molecular weight of 100,000 to 5,000,000; wherein the pain treating effective amount of the drug composition is at least 1 mg of drug in the solid drug reservoir; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. Preferably the medical device used in the methods of inducing and maintaining analgesia, further comprises a backing layer having a top side and a bottom side, wherein the solid drug reservoir layer has a top side and a bottom side and an external edge; the bottom side of the backing layer is contiguously disposed to the top side of the solid drug reservoir layer; and the external edge of the solid drug reservoir layer is not completely sealed by the backing layer. In some embodiments, in the medical device used in the methods of the invention, the solid drug reservoir layer has a top side and a bottom side, and: at least 2% w/w of the solid drug reservoir layer is drug and no more than 15% w/w of the solid drug reservoir layer is drug; at least 70% w/w of the solid drug reservoir layer is polydimethylsiloxane matrix material; and at least 5% w/w of the solid drug reservoir is polydimethylsiloxane plasticizer and no more than 6% w/w of the solid drug reservoir is polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl. In some embodiments, the medical device further comprises: a backing layer having a top and a bottom side, wherein the bottom side of the backing layer is contiguously disposed with respect to the top side of the solid drug reservoir layer; and a rate controlling membrane having a top and a bottom side; wherein the top side of the rate controlling membrane is contiguously disposed with respect to the bottom side of the drug reservoir layer; wherein the rate controlling membrane comprises: one or more compositions selected from the group consisting of: low density polyethylene, polyethylene-(vinyl acetate) copolymer, heat sealable polyester and elastomeric polyester block copolymer; a polyethylene-(vinyl acetate) copolymer with up to 33% vinyl acetate, the copolymer having a molecular weight of 10,000 or greater; the thickness and vinyl acetate composition of the rate controlling membrane are selected to provide a 0.5 to 10 µm/cm$^2$hr permeation rate through the rate controlling membrane at 32 degrees C.; and an adhesive layer having a top and a bottom side; wherein the top side of the adhesive layer is contiguously disposed with respect to the bottom side of the rate controlling membrane; wherein the adhesive layer is adapted to be maintained in drug-transferring relationship to the human skin; wherein: at least 5% w/w and no more than 6% w/w of the adhesive layer is polydimethylsiloxane plasticizer, wherein the polydimethylsiloxane plasticizer is dimethicone with a viscocity of 20 to 12,500 centistoke; and at least 70% w/w of the adhesive layer is polydimethylsiloxane matrix material, wherein the polydimethylsiloxane matrix material has a molecular weight of 100,000 to 5,000,000. In some embodiments, at least 4.5% w/w of the solid drug reservoir layer is drug and no more than 5% w/w of the solid drug reservoir layer is drug; at least 5% w/w of the solid drug reservoir layer is polydimethylsiloxane plasticizer and no more than 6% w/w of the solid drug reservoir layer is polydimethylsiloxane plasticizer; and at least 5% w/w of the adhesive layer is polydimethylsiloxane plasticizer and no more than 6% w/w of the adhesive layer is polydimethylsiloxane plasticizer; wherein the drug is selected from the group consisting of fentanyl, oxymorphone, oxycodone, hydromorphone, porphine, buprenorphine and analgesically effective derivatives thereof, preferably fentanyl and analgesically effective fentanyl derivatives, most preferably fentanyl.

BRIEF DESCRIPTION OF THE DRAWINGS

There are shown in the drawings certain exemplary embodiments of the present invention as presently preferred. It should be understood that the present invention is not limited to the embodiments disclosed as examples, and is capable of variation within the spirit and scope of the appended claims.

In the drawings.

GLOSSARY

Figure 1:
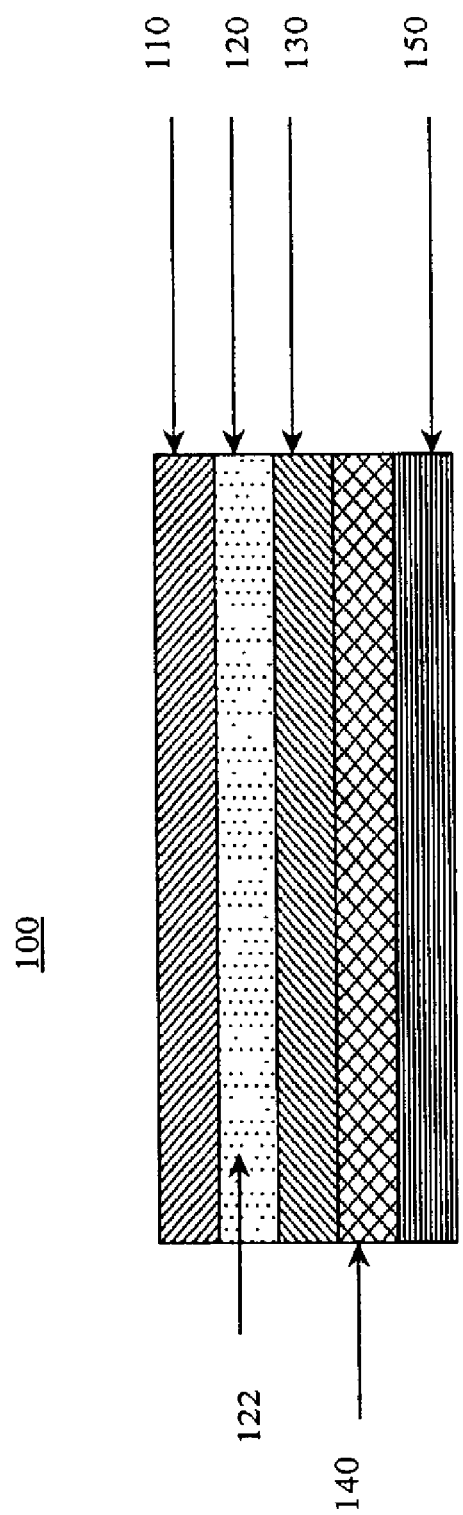
FIG. 1 is a schematic illustration of a solid reservoir transdermal drug delivery device of the present invention.

The following definitions are provided to facilitate an understanding of certain terms used frequently herein.

The term "administration period" means the time period during which the delivery device releases an active agent or combination of active agents to a subject.

The terms "drug" and "drug composition" as used interchangeably herein mean fentanyl, oxymorphone, oxycodone, hydromorphone, morphine, buprenophine and analgesically effective derivatives thereof.

The term "drug reservoir" means a composition made to retain and release a drug for transdermal delivery, which composition is produced by combining a drug and a matrix material. The drug reservoir can be a drug reservoir composition, a solid drug reservoir layer, a solid drug reservoir adhesive layer, or a liquid drug reservoir layer. In some embodiments, a drug reservoir can be a solid drug reservoir layer in a multilaminate transdermal drug delivery medical device. When combined with an adhesive, the drug reservoir can also be a solid drug reservoir adhesive layer, which can be used, for example, in a monolith tranderrmal drug delivery medical device. The drug reservoir can also comprise permeation enhancers, plasticizers, and any other suitable additive, unless otherwise noted.

The term "drug transferring effective relationship" means that a device adapted for transdermal administration of a drug is kept in sufficient contact with the skin of a subject to allow for transdermal entry of the drug.

The terms "effective amount" and "therapeutically effective amount" mean a nontoxic but sufficient amount of a compound to provide the desired local or systemic therapeutic effect.

The term "fentanyl composition" means fentanyl, or any pharmaceutically acceptable derivative or salt thereof. Accordingly, the term "fentanyl composition" refers to fentanyl (chemical name: N-Phenyl-N-(1-[2-phenylethyl]-4-piperidinyl)propanamide; CAS No. 990-73-8), its analgetically effective derivatives (hereafter referred to as "derivatives") such as sufentanyl, carfentanyl, lofentanyl and alfentanyl, and to any pharmaceutically acceptable salt of any of the foregoing.

The term "flux" means the in vitro rate of delivery of drug per unit area through an area of human cadaver skin at 32 degrees C.

The term "flux rate lowering effective amount" means an amount of a composition, for example a plasticizer, effective to lower the drug flux rate out of a medical device to a lower maximum flux rate than that achieved when the plasticizer composition is not present at all. Flux rates can be measured through human cadaver skin at 32 deg. C. in accordance with the procedure described in Example 1.

The term "monolith" means a transdermal medical device wherein the drug reservoir layer comprises a drug for transdermal administration and an adhesive composition that maintains the medical device in transdermal drug administration permitting contact with the skin. In some embodiments, the monolith is a drug reservoir adhesive layer comprising a drug composition, an adhesive composition and a matrix composition.

The term "multilaminate" refers to a transdermal medical device that comprises at least two layers, including a drug reservoir layer. In some embodiments, the multilaminate transdermal medical device can comprise a solid drug reservoir layer, a rate controlling membrane layer, a backing layer and an adhesive layer.

The term "solid drug reservoir" means a drug reservoir that comprises less than 1% w/w of any solvent used in producing the drug reservoir composition, and preferably less than 100 ppm. For example, in some embodiments, the solid drug reservoir produced using heptane and isopropyl alcohol comprises less than 100 ppm heptane and less than 100 ppm alcohol in the solid drug reservoir.

The term "permeation enhancer" means a natural or synthetic molecule which facilitates the absorption of a given active agent or combination of active agents through tissue.

The term "pressure-sensitive adhesive" refers to a viscoelastic material which adheres to substrates with the application of pressure and remains permanently tacky.

The term "subject" means an animal, preferably a mammal, more preferably a human.

The term "sustained release" means the continual release of an active agent or combination of active agents over a period of time.

"Thickness" unless otherwise indicated is measured in mils (a mil=one thousandth of an inch) and can be determined by measuring the spacing when a transdermal delivery medical device of the present invention is placed between two microscopic slides.

"Transdermal" or "percutaneous" delivery means delivery of a drug by passage into and through the skin, and/or other body surfaces as a portal for the administration of drugs by topical application of the drug thereto.

The term "solvent content" is the percent residual process solvent (e.g., water, heptane, isopropyl alcohol) per unit dose as measured to the Karl Fisher method (for water) or appropriate analytical techniques (such as gas chromatograph, and the like) and expressed as percent of the weight of a delivery device of the present invention.

DETAILED DESCRIPTION

The present invention will now be further described through the following detailed description of the present invention, which detailed description is illustrative of the preferred embodiments of the present invention and is not intended to limit the scope of the invention as set forth in the appended claims. While the following detailed description describes the invention through reference to embodiments of the present invention utilizing fentanyl and analgesically effective derivatives thereof as the drug, it should be understood that other drugs are also suitable for use with the teachings of the present invention including: oxymorphone, oxycodone, hydromorphone, morphine, buprenorphine and analgesically effective derivatives thereof.

Figure 4:
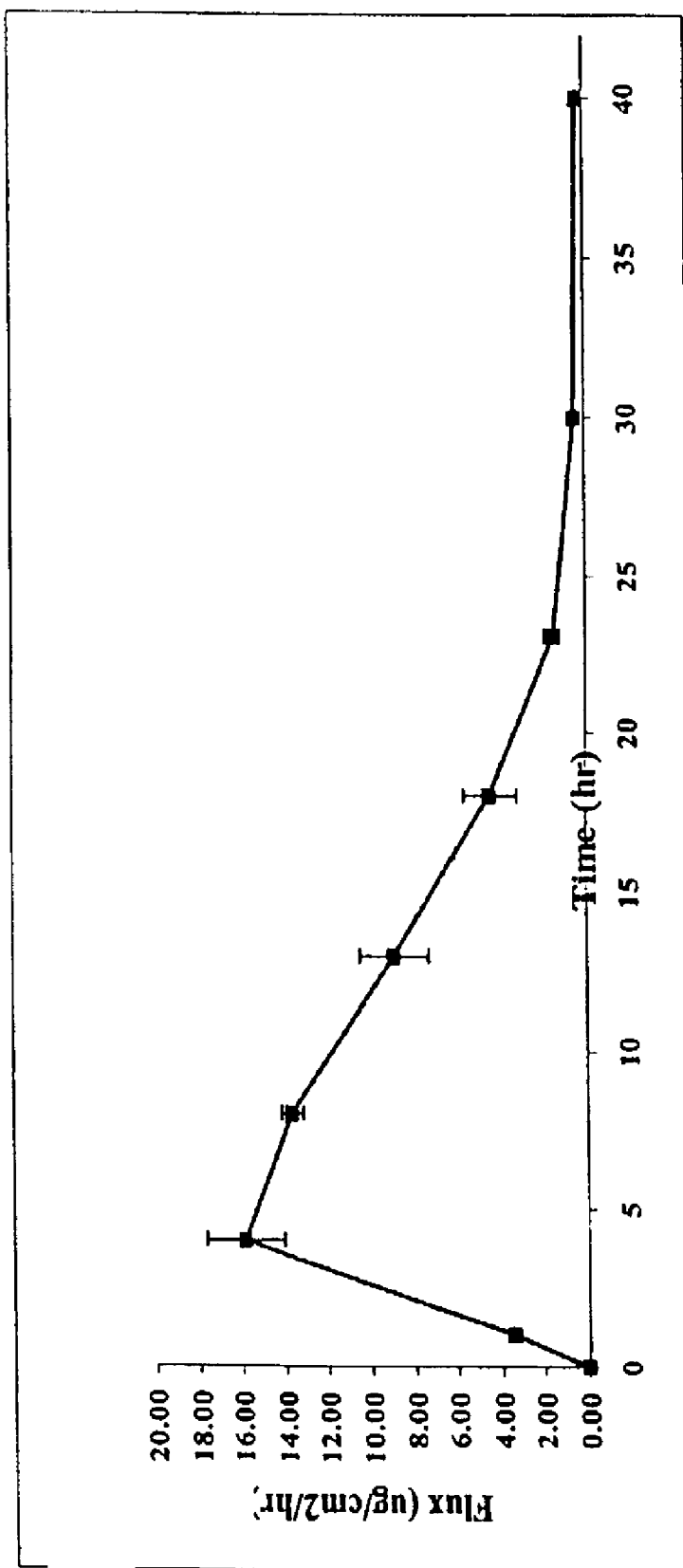
FIG. 4 is a graph of the permeation profile of fentanyl from a transdermal medical device with a plasticizer loading that is greater than a fentanyl flux rate lowering effective amount.
Figure 5:
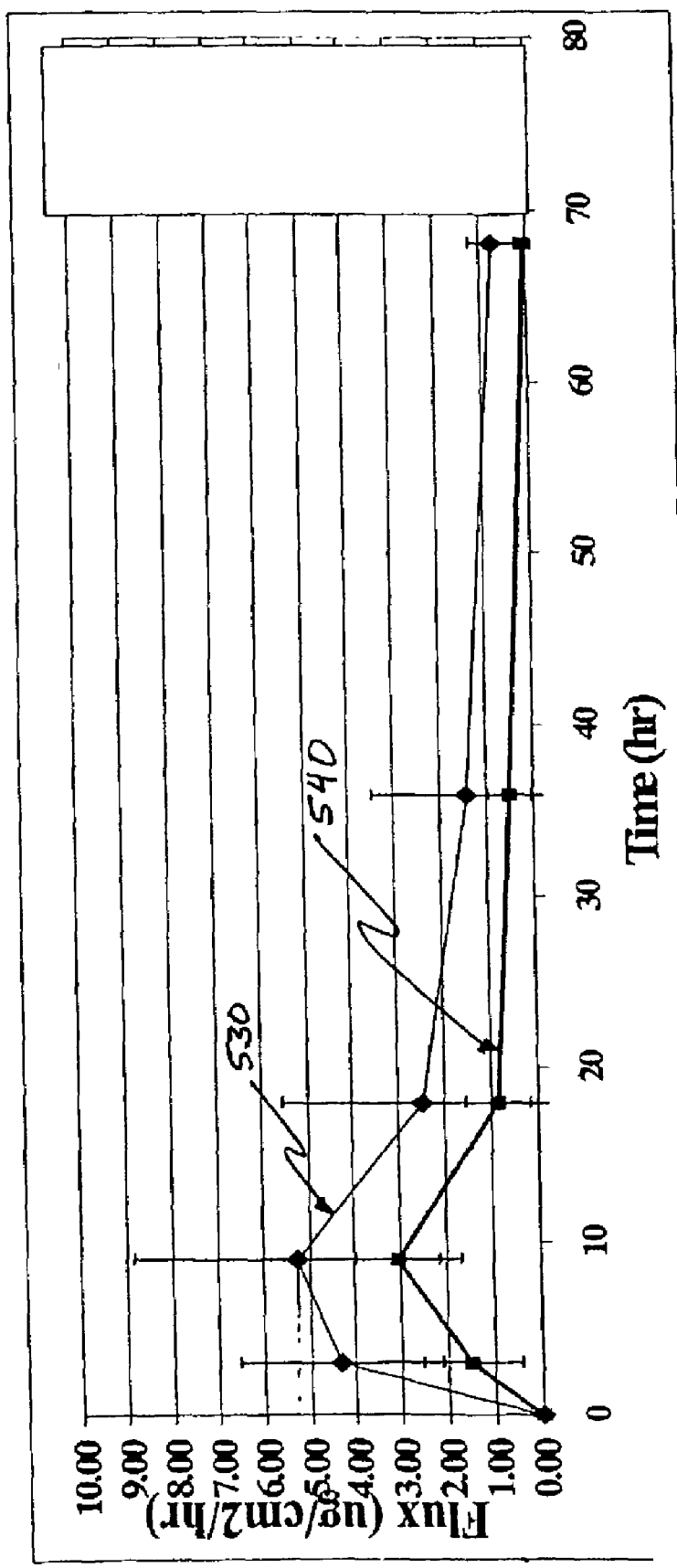
FIG. 5 is a graph comparing the permeation profiles showing fentanyl flux rates from two different transdermal medical devices.

In one embodiment of the invention, compositions are provided that comprise a matrix material and a drug flux rate changing effective amount of a suitable plasticizer, preferably a fentanyl flux rate lowering effective amount of the suitable plasticizer. In preferred embodiments, a suitable plasticizer is a fentanyl flux rate lowering effective amount of a drug flux rate lowering plasticizer. Combining a drug flux rate lowering effective quantities of certain drug flux rate lowering plasticizers with particular types of matrix compositions will surprisingly lower, rather than raise, the drug flux rate from a transdermal medical device comprising the composition. Furthermore, either omitting the drug flux rate lowering plasticizer completely from the matrix composition, or adding more than a drug flux rate lowering effective amount of a drug flux rate lowering plasticizer to the same matrix composition, can result in an increase in the drug flux rate from the medical device comprising a drug flux rate lowering amount of a drug flux rate lowering plasticizer to a matrix composition. For example, in one embodiment, the fentanyl flux rate of a particular transdermal delivery patch was about 3 μg/cm$^2$hr (for example, graph 500 of FIG. 5 showing a fentanyl flux rate lowering effective plasticizer loading 540). By comparison, when more than a fentanyl flux rate lowering effective amount of plasticizer was added to the same type of patch system, the fentanyl flux rate of a particular transdermal delivery patch was about 16 μg/cm$^2$hr (for example, graph 400 of FIG. 4 showing the relation measured between the fentanyl flux rates as a function of time 440). When less than a fentanyl flux rate lowering effective amount of plasticizer was added to the same type of patch system, the fentanyl flux rate of a particular transdermal delivery patch was about 5 μg/cm$^2$hr (for example, graph 500 of FIG. 5 showing the relation measured between the fentanyl flux rates as a function of time 530). Accordingly, Applicant has discovered a window of drug flux rate lowering effective amounts of certain plasticizers when combined with certain matrix materials. Compositions of the present invention can be used to form drug reservoir layers, drug reservoir adhesive layers or adhesive layers in medical devices for transdermal administration of fentanyl compositions.

The matrix material of the compositions of the invention can comprise a material that can be used for construction of a transdermal drug delivery device that allows for the lowering of the fentanyl flux rate when a flux rate lowering effective amount of a suitable plasticizer is added to the matrix material, as compared to the fentanyl flux rate when the suitable plasticizer is omitted or added in an amount greater than a flux rate lowering amount. In some embodiments, the invention provides a matrix material that is an amine resistant adhesive. Preferably, the matrix material is an amine resistant silicone adhesive. Examples of suitable amine resistant silicone adhesive matrix material compositions include any type of "high tack" polydimethylsiloxane with an average molecular weight of between 100,000 and 5,000,000, preferably 500,000 and 1,500,000.

In a particularly preferred aspect, the invention provides that adding a plasticizer to the matrix material composition can lower the fentanyl flux rate from a transdermal medical device of the invention. Accordingly, a fentanyl flux rate lowering effective amount of the plasticizer is preferably incorporated into the matrix material compositon. Particularly preferred plasticizers include low molecular weight polydimethylsiloxane described in the National Formulary as Dimethicone with a viscosity of between 20 and 12,500 centistoke, and preferably between 300 and 400 centistoke. For example polydimethylsiloxane plasticizer with an average molecular weight of about 9800 with a viscosity of between 330 and 370 centistoke can be used in some embodiments of the invention. In some embodiments, the fentanyl flux rate lowering amount is greater than about 3% w/w and up to about 20% w/w of the composition, preferably less than 10% w/w. Most preferred are matrix material compositions comprising 4 to 7% w/w plasticizer. In some embodiments, the plasticizer may also improve the adhesive characteristics of a dermal composition.

The plasticizer employed is preferably compatible with the matrix material. For example, in some preferred embodiments, when the matrix materials comprises polysiloxane as a major component, the plasticizer can be silicone fluid (e.g., 360 Medical Fluid, available from Dow Corning Corporation, Midland, Mich.).

The compositions of the invention can be used, for example, as a solid drug reservoir or as an adhesive portion of any transdermal drug delivery device. In some embodiments, the compositions of the invention can be used as a part of a multilaminate medical device, or as part of a monolithic medical device. In some embodiments, the compositions of the invention are pressure-sensitive compositions for use in transdermal drug delivery devices. The principles of the invention would still apply to embodiments where the composition is not a pressure-sensitive adhesive and comprises the drug reservoir.

In some embodiments, one or more drug reservoir layers can be made from the compositions of the invention. Accordingly, the composition of the invention may further comprise a theraputically effective amount of a drug dissolved or suspended therein. Preferably, the drug is a fentanyl composition present in a drug delivery device of the invention in a therapeutically effective amount, i.e., an amount effective to bring about a desired therapeutic result in the treatment of a condition. The amount that constitutes a therapeutically effective amount varies according to the particular drug incorporated in the device, the condition being treated, any drugs being coadministered with the selected drug, desired duration of treatment, the surface area of the skin or mucosa over which the device is to be placed, and other components of the drug delivery device that can be determined by one skilled in the art for a particular embodiment. In preferred embodiments, the drug is fentanyl or its analgetically effective derivatives (hereafter referred to as "derivatives") such as sufentanyl, carfentanyl, lofentanyl and alfentanyl.

In general, therapeutic amounts of fentanyl drug in a solid drug reservoir composition can be delivered from a composition (for example, a solid drug reservoir composition or a solid drug reservoir adhesive composition) containing 0.1% or at least 0.1 mg, to about 10% by weight of drug or no more than about 30 mg, or more preferably from about 1% to about 6% by weight. However, the composition of this invention is particularly useful for drugs which are used in relatively low concentrations, especially 4% to 6% of the total composition, provided the medical device comprising the solid drug reservoir composition of the invention comprises at least 1.0 mg of fentanyl or a pharmaceutically appropriate derivative.

In some embodiments, the invention provides medical devices for the transdermal administration of a fentanyl composition that comprise the fentanyl flux rate lowering compositions of the invention. Preferably, the medical devices of the invention comprise a solid drug reservoir that can be attached to other materials, including but not limited to, a backing material, a strippable/disposable release liner, an adhesive material and/or a rate controlling membrane. It is understood that the drug reservoir of a medical device of the invention can, of course, be contacted by other types of materials and layers, as appropriate to one practicing in the art.

Backing materials are well known in the art and can comprise plastic films of polyethylene, vinyl acetate resins, ethylene/vinyl acetate copolymers, polyvinyl chloride, polyurethane, and the like, metal foils, non-woven fabric, cloth and commercially available laminates. The backing material generally has a thickness in the range of 2 to 1000 micrometers. In preferred embodiments, the backing material is substantially impermeable to the drug contained in the drug reservoir layer, as well as the other contents of the drug reservoir layer. For example, a backing material can comprise a multilaminate of polyethylene terephthalate (PET) and polyethylene-(vinyl acetate) (EVA) copolymer. Numerous examples of appropriate backing materials are recognized in the art. Some nonlimiting, specific examples of backing materials include: (1) a PET backing material with a sealable layer of EVA (e.g., 12% vinyl acetate, VA) coated on one side of the PET backing material; (2) a 7-layer filme comprising low density PET, nylon, EVA, and ethylene vinyl alcohol; (3) a 4-layer film comprising low density polyethylene, nylon and EVA; (4) a bi-layer film comprising low density polyethylene and nylon; (5) a monolayer of polyethylene polymer material; or (6) a monolayer of PET.

Various suitable strippable release liners are also well known in the art and include a fluoropolymer (for example, fluorocarbon diacrylate) or silicone (polysiloxane polymers) coated polyester film produced at a nominal thickness of about 3 mils. Examples of suitable commercially available release liners include a 5 mil fluoropolymer coated polyester film manufactured by 3M (Minnesota, Minn.) sold as S$_{cotch-pak}$ 9742™. It is also possible to use films made of material other than polyester or polyethylene terephthalate (PET), with a fluoropolymer coating. For example, the film can also be made of polystyrene or polypropylene. The same materials can also be used with a different coatings such as silicone. For preferred embodiments in which a polysiloxane is part of the multiple polymeric adhesive system, the release liner must be compatible with the silicone adhesive. In certain preferred embodiments of the invention, a suitable commercially available liner is 3M's 1022 S$_{cotchpak}$™, a fluoropolymer (fluorocarbon diacrylate) coated polyester film produced at about 3 mils thickness.

Preferably, the medical devices of the invention comprise a solid drug reservoir wherein at least a portion of the peripheral edges remains unsealed. The term "peripheral edge" of the drug reservoir and backing layer refer to the areas around the edges, that would be sealed together to define a liquid or gel based drug reservoir. Unlike medical devices comprising a liquid or gel drug reservoir, the solid drug reservoirs of the medical devices of certain embodiments of the present invention need not be entirely sealed around their peripheral edges. The peripheral edges of a liquid or gel drug reservoir layer should be substantially fluid-tight to prevent drug leakage from the reservoir through the seal between the backing layer and the membrane. In some embodiments, the medical devices of the invention comprise a solid drug reservoir with peripheral edges that are not covered by a backing layer. In preferred embodiments, the medical devices of the invention that comprise a solid reservoir layer do not present a hazard of drug leakage if the patch is torn, and do not need to be sealed to ensure against leaking. Avoiding the need for sealing of the drug reservoir layer can potentially lower production costs by avoiding one or more additional industrial processing steps.

In some embodiments, the medical devices of the invention can further comprise a rate-controlling membrane. Rate controlling membranes are preferably 0.5 to 10 mils thick, preferably 1-5 mils thick, and can be comprised of, for example, low density polyethylene (LDPE), EVA copolymers (for example, with up to 40% w/w and preferably between about 5 and 19% w/w VA), heat sealable polyesters, elastomeric polyester block copolymers, PVC and the like.

Preferably, the composition of the rate control membrane can be selected in conjunction with a certain flux lowering composition in the drug reservoir layer. Preferably, the rate-controlling membrane comprises a polyethylene(vinyl acetate) copolymer with up to 33% vinyl acetate in a polyethylene(vinyl acetate) copolymer, and more preferably about 19% w/w vinyl acetate, the copolymer preferably having a high molecular weight (about 9,000 or greater). One skilled in the art would recognize that when the rate-controlling membrane comprises polyethylene-(vinyl acetate), the membrane thickness and the vinyl acetate content of the copolymer independently affect the flux of the drug passing through the membrane. The flux increases as the thickness decreases and the flux decreases as the thickness increases. The flux increases as the vinyl acetate content increases and the flux decreases as the vinyl acetate content decreases.

By way of example, in some embodiments, similar fentanyl flux rates can be obtained from medical devices comprising a solid drug reservoir and a high molecular weight (e.g., greater than 9,000) polyethylene and VA rate controlling membrane of any of the following combinations of thickness and vinyl acetate content: (1) a thickness of 4 mils and a VA content of 19% w/w; (2) a thickness of 2 mils and a VA content of 9% w/w; (3) a thickness of 1 mil and a VA content of less than 9%; or (4) a thickness of 6 mils and a VA content of greater than 19% w/w. Graphical representations of permeability of such commercially available membranes vs. percent vinyl acetate composition, or moisture vapor transmission rates vs. percent polyethylene-(vinyl acetate) copolymer composition are readily available from commercial vendors. Accordingly, the dimensions and composition of the rate control membrane can be selected to provide a desired fentanyl flux rate from a medical device for transdermal delivery.

In some embodiments, the rate controlling membrane can comprise a microporous or porous material. Microporous membranes have a distinct pore structure with pores ranging in diameter from approximately 0.08 to 0.5 microns, preferably from about 0.1 and 0.4 microns, and more preferably from about 0.2 and 0.4 microns. Examples of suitable microporous membranes include polyethylene and polypropylene films, nylon, and nitrocellulose film. A preferred membrane material is C$_{otran}$® 9716, which is a 4 mils thick polyethylene-(vinyl acetate) copolymer membrane with 19% w/w vinyl acetate, available from 3M Corporation. Other embodiments of the present invention will utilize microporous polyethylene membranes, such as Celgard K-256, available from Hoechst-Celanese, Charlotte, N.C. Porous membranes have pores greater than about 3 microns in diameter. Such materials are available as woven and non-woven fabrics. These materials can also be fabricated from nylon, polypropylene, polyethylene, polyolefins and the like.

The configuration of the transdermal delivery systems of the present invention can be in any shape or size as is necessary or desirable. Illustratively, a single dosage unit may have a surface area in the range of 1 to 200 cm$^2$ Preferred sizes are: from 5 to 60 cm$^2$.

In some embodiments, the matrix compositions of the transdermal drug delivery system can, optionally, also contain agents known to accelerate the delivery of the drug through the skin. These agents have been referred to as skin-penetration enhancers, accelerants, adjuvants, and sorption promoters, and are collectively referred herein as "permeation enhancers." This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug.

Permeation enhancers suitable for use with the present invention include, but are by no means limited to, a natural or synthetic molecules which facilitate the absorption of an active agent through a mucosal tissue. Some examples of permeation enhancers are polyhydric alcohols such as dipropylene glycol, propylene glycol and polyethylene glycol which enhance drug solubility; oils such as olive oil, squalene, and lanolin; fatty ethers such as cetyl ether and oleyl ether; fatty acid esters such as isopropyl myristate which enhance drug diffusibility; urea and urea derivatives such as allantoin which affect the ability of keratin to retain moisture; polar solvents such as dimethyldecylphosphoxide, methyloctyl-sulfoxide, dimethyllaurylamide, dodecylpyrrolidone, isosorbitol, dimethyl-acetonide, dimethylsulfoxide, decylmethyl-sulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, isopropyl palmitate and glyceryl monooleate.

The medical devices of the invention may further be provided with various thickeners, fillers and other additives known for use with dermal compositions. Where the composition tends to absorb water, for example, when lecithin is used as a co-solvent, hydrophilic fillers are especially useful.

While some preferred device aspects of the invention are generally described above, the invention can be further illustrated with respect to certain selected embodiments illustrated in the Figures and presented below. The selected embodiments discussed below are included for illustrative purposes and are not intended, and should in no way be construed to, limit the scope of the generally described invention.

In some embodiments, the present invention provides a multilaminate medical device. Referring to FIG. 1, a schematic illustration of a multilaminate transdermal drug delivery device 100 embodiment of the present invention comprises a backing layer 110, a drug reservoir layer 120, a rate controlling membrane 130, an adhesive layer 140 and a strippable release liner 150. The backing layer 110 can be any backing layer described above, such as a 1-5 mil thick multilaminate comprising PET and EVA. In some embodiments, the backing layer 110 can be impermeable to liquids from outside medical device. The solid drug reservoir layer 120 comprises a matrix material such as an amine resistant silicone adhesive and a fentanyl flux rate lowering amount of one or more suitable plasticizer(s) such as polydimethylsiloxane (e.g., Medical Fluid 360 from Dow Corning). The solid drug reservoir composition also has a dissolved and suspended drug within the solid drug reservoir layer 120. Preferably, the drug composition is fentanyl, a fentanyl derivative, or a pharmaceutically acceptable salt thereof. The peripheral edge 122 of the solid drug reservoir layer 120 is unsealed, and can be exposed to air, in the medical device product of the invention shown in FIG. 1. The rate controlling membrane 130 comprises low density polyethylene, polyethylene-(vinyl acetate) copolymers (with up to 40% vinyl acetate, preferably between 5 and 19% vinyl acetate, and most preferably 19% vinyl acetate). The thickness of the rate controlling membrane 130 can be adjusted with the percent vinyl acetate in the composition to provide a selected fentanyl flux rate, as discussed above. The rate controlling membrane 130 is between about 0.5 to 5.0 mils (that is, about 0.0127 to 0.1270 inches) thick. The adhesive layer 140 is comprised of the same matrix material composition and a similar type of flux rate lowering plasticizer as the solid drug reservoir composition 120. The adhesive layer 140 comprises a flux rate lowering effective amount of the plasticizer(s) present in the solid drug reservoir layer 120. Most preferably, the adhesive layer 140 comprises the same plasticizer(s) present in the solid drug reservoir layer 120 in approximately the same weight percentage(s). The strippable release liner 150 can be any release liner described above, such as a 3 mil thick fluorocarbon diacrylate or silicone (polysiloxane) coated polyester film. The various layers are laminated or otherwise assembled into a transdermal drug delivery device, such as a bandage or patch, having a medically appropriate predetermined size and shape as known in the art. While FIG. 1 describes a preferred embodiment, it should be recognized that one or more of the layers may be deleted or repeated, the basic trnasdermal system being a drug containing matrix material comprising the fentanyl flux rate lowering composition of the invention provided and maintained in drug transferring effective relationship with the skin. In particularly preferred embodiments comprising both an adhesive layer 140 and a solid drug reservoir layer 120, both layers preferably comprise matrix materials and plasticizer(s) that are similar in type and amount.

Figure 2:
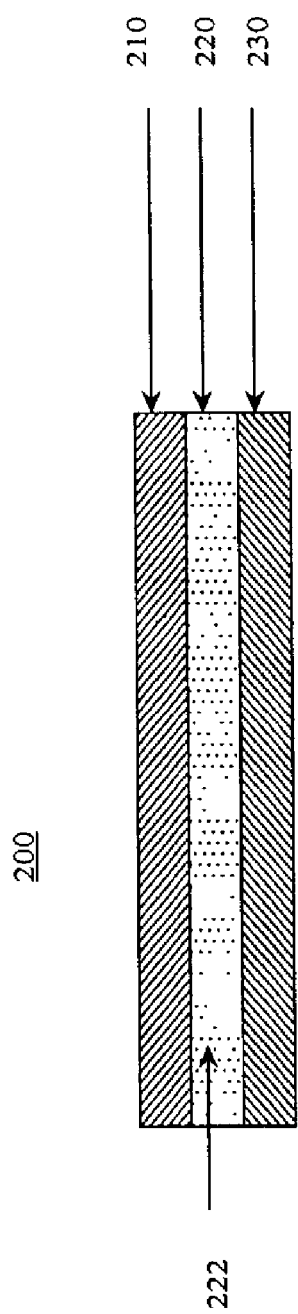
FIG. 2 is a schematic illustration of a monolith transdermal drug delivery device of the present invention.

FIG. 2 is a schematic illustration of a monolith medical device 200 for transdermal drug delivery. Such a medical device 200 comprises a backing layer 210, a drug reservoir adhesive layer 220 and a strippable release liner 230. The backing layer 210 can be any backing layer described above, such as a 1-5 mils thick multilaminate comprising PET and EVA. In some embodiments, the backing layer 210 can be impermeable to liquids from outside medical device. The drug reservoir adhesive layer 220 comprises a matrix material such as an amine resistant silicone adhesive and a fentanyl flux rate lowering amount of one or more suitable plasticizer(s) such as a polydimethylsiloxane emulsion (e.g., Medical Fluid 360 from Dow Corning). For example, the drug reservoir adhesive layer 220 can comprise about 70-95% w/w of a polysiloxane-based adhesive matrix material, about 4-20% w/w polydimethylsiloxane-type plasticizer and about 2-15% w/w of the fentanyl drug composition. The drug reservoir adhesive layer 220 in a monolith medical device 200 can serve as both a solid drug reservoir and as an adhesive layer to maintain the monolith medical device 200 in transdermal drug flux permitting contact with a subject's skin throughout an administration period. The drug reservoir adhesive layer 220 composition has a dissolved and suspended drug within the drug reservoir adhesive layer 220. Preferably, the drug composition is fentanyl, a fentanyl derivative, or a pharmaceutically acceptable salt thereof. The peripheral edge 222 of the drug reservoir adhesive layer 220 is unsealed, and can be exposed to air, in the medical device product of the invention shown in FIG. 2.

In one aspect of the invention, Applicant has discovered a window of flux rate lowering effective amounts of certain plasticizers with certain matrix materials. Thus, combining a flux rate lowering effective quantities of certain flux rate lowering plasticizers with particular types of matrix compositions will surprisingly lower, rather than raise, the drug flux from a transdermal medical device comprising the composition. Furthermore, either omitting the flux rate lowering plasticizer completely from the matrix composition, or adding more than a flux rate lowering effective amount of a flux rate lowering plasticizer to the same matrix composition, can result in an increase in the flux rate of drug delivery from the medical device comprising a flux rate lowering amount of a flux rate lowering plasticizer to a matrix composition.

This fentanyl flux rate lowering effect, achieved by adding a flux rate lowering effective amount of a suitable plasticizer to a matrix material according to the invention, can be demonstrated, for example, by comparing in vitro drug flux rates of fentanyl compositions from multilayer transdermal medical devices, for example fentanyl patches, comprising varying amounts plasticizer in the drug reservoir layer and adhesive layer. FIGS. 3 to 6 illustrate this aspect of the invention below. The in vitro drug flux rates of fentanyl compositions through human cadaver skin in vitro at 32 degrees C. can be obtained according to the procedure described in the Examples below. FIG. 3, FIG. 4, FIG. 5, and FIG. 6A are provided using a fentanyl patch comprising a polydimethylsiloxane matrix material and a polydimethyl siloxane plasticizer.

Figure 3:
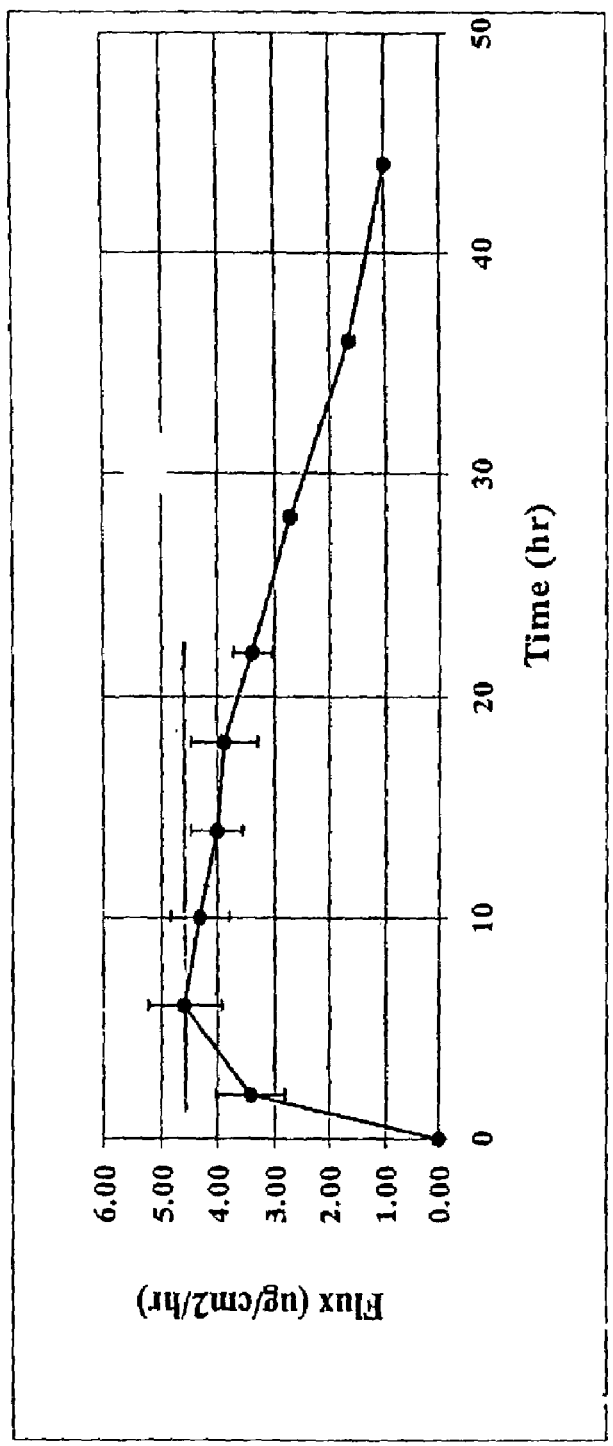
FIG. 3 is a graph of the permeation profile of fentanyl from a transdermal medical device without any plasticizer loading.

FIG. 3 is a graph of the permeation profile of fentanyl from a transdermal medical device without any plasticizer loading (i.e., a plasticizer loading that is less than a fentanyl flux rate lowering effective amount). Specifically, FIG. 3 provides a graphical representation of the fentanyl flux rate from the medical device, in $\mu g/cm^2$, as a function of time, in hours. FIG. 4 is a graph of the permeation profile of fentanyl from a transdermal medical device with a plasticizer loading that is greater than a fentanyl flux rate lowering effective amount. The graph shows fentanyl flux rates as a function of time, as measured through cadaver skin in vitro at 32 deg. C., as a comparative example. Specifically, FIG. 4 provides a graphical representation of the fentanyl flux rate from the medical device, in $\mu g/cm^2$, as a function of time, in hours. FIG. 5 is a graph comparing fentanyl flux rates from two different transdermal medical devices: a transdermal medical device of the invention comprising a fentanyl flux rate lowering effective plasticizer loading (the curve labeled 540) and a comparative example of a transdermal medical device with less than the flux rate lowering effective amount of plasticizer (the curve labeled 530). The curves in FIG. 5 depict fentanyl flux rates, in $\mu g/cm^2$ as a function of time in hours, as measured through cadaver skin in vitro at 32 deg. C. As shown by the noted graphs, the fentanyl flux rate is greater when more than a flux rate lowering effective amount of plasticizer is added to the matrix material, FIG. 4, or when less than a flux rate lowering effective amount of plasticizer is added to the matrix material, FIG. 3 and curve 530 in FIG. 5, than when a flux rate lowering effective amount of plasticizer is added to the matrix material, curve 540 in FIG. 5.

Figure 6:
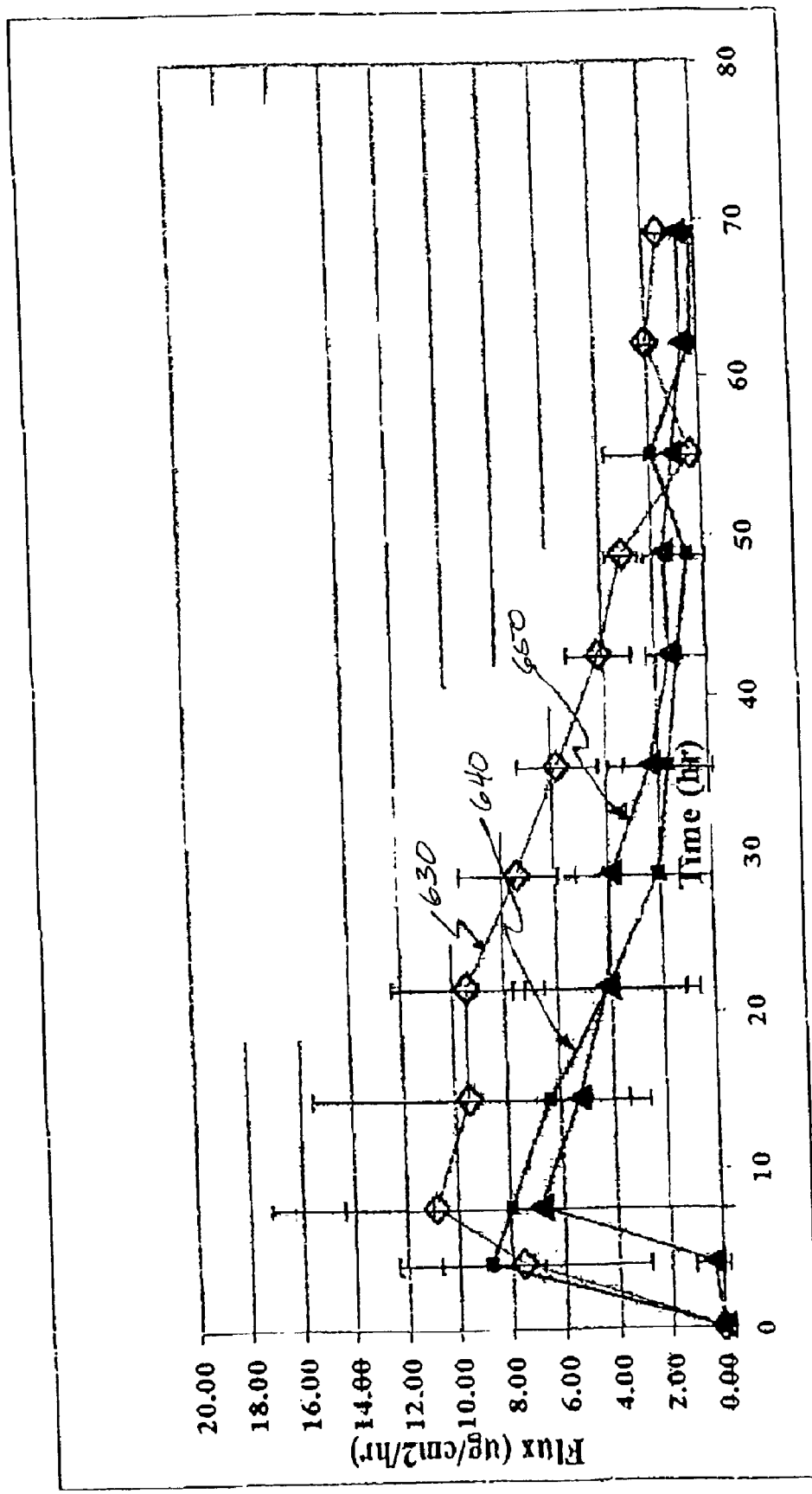
FIG. 6 displays several graphs comparing the permeation profiles showing fentanyl flux rates from different transdermal medical devices.

In some embodiments, the invention provides a range of flux rate lowering effective amounts of plasticizer(s). FIG. 6 presents three curves comparing the permeation profiles showing fentanyl flux rates, in $\mu g/cm^2$ as a function of time in hours, from three different transdermal medical devices: a first transdermal medical device of the invention comprising a first fentanyl flux rate lowering effective plasticizer loading permeation profile (curve 640), a second transdermal medical device of the invention comprising a second fentanyl flux rate lowering effective plasticizer loading permeation profile (curve 650) and a comparative example of a permeation profile from a transdermal medical device with less than the flux rate lowering effective amount of plasticizer (curve 630). The curves in FIG. 6 show fentanyl flux rates as a function of time, as measured through cadaver skin in vitro at 32 deg. C. In some embodiments, the first fentanyl flux rate lowering effective plasticizer loading permeation profile depicted in curve 640 corresponds to a 5% w/w plasticizer loading in a solid drug reservoir layer, the second fentanyl flux rate lowering effective plasticizer loading permeation profile depicted in curve 640 corresponds to a 6% w/w plasticizer loading in a solid drug reservoir layer, and the permeation profile from the transdermal medical device with less than the flux rate lowering effective amount of plasticizer depicted in curve 630 corresponds to a 0.1% w/w plasticizer loading.

While many of the preferred embodiments of the invention are directed to fentanyl-containing transdermal delivery patches, the invention is not limited to patch devices. As appreciated by one skilled in the art, a variety of fentanyl-containing transdermal delivery devices can be made and used in accordance with the present invention. Such fentainyl containing transdermal delivery devices are not limited to the form of the article and include, but are not limited to, articles such as a tape, a patch, a sheet, a dressing or any other form known to those skilled in the art. Generally the device will be in the form of a patch of a size suitable to deliver a preselected amount of fentanyl or other drug through the skin.

One skilled in the art given the above description of the compositions for solid drug reservoir layers or drug reservoir adhesive layers in various medical devices of the present invention will be able to produce those devices using a variety of known processing methods. Preferably, the compositions for making solid drug reservoir layers and drug reservoir adhesive layers of the present invention are produced using the following described process.

Applicant has surprisingly discovered that addition of an alcohol dispersing agent to the drug composition maintains greater uniformity of drug distribution in a mixture of drug, solvent, and matrix adhesive prepared during manufacture of the solid drug reservoir layer than physical agitation of a mixture of the matrix material and the drug composition. Accordingly, a preferred method for preparing the drug-containing compositions of the present invention involves:

A. The adhesive is received in a solution with a solvent. Alternatively, the adhesive and solvent may be received separately, and dissolution of the adhesive in the solvent will be an additional step in the process. The plasticizer is added at the proper ratio to the adhesive solution so that when the solvent is removed by evaporation the plasticizer will be present in the dried adhesive at the correct concentration.

B. The fentanyl is dispersed in a suitable alcohol dispersing agent, or other appropriate solvent, by weighing the fentanyl in a suitable container, adding the alcohol, and swirling or mixing with an agitator or other suitable means of mixing. The ratio of fentanyl to alcohol is in the range of 1:1 to 1:10, preferably 1:1 to 1:3.

C. The dispersion of fentanyl in alcohol is then mixed with the adhesive/plasticizer mixture and mixed with an agitator, or other suitable means of mixing, for a time ranging from 5 minutes to 10 hours, preferably 30 minutes to 120 minutes. This mixture of fentanyl, alcohol, adhesive, plasticizer, and solvent may be stored for up to one week before the subsequent processing is conducted. Remixing for a short period, up to 90 minutes, may be performed if the mixture is stored for a period prior to the subsequent processing step.

D. The mixture is metered through a casting die, or other suitable device for depositing the mixture, at a uniform thickness onto a moving web of protective liner. The web passes through an oven with several zones at several different temperatures and several different air flow rates at a linear rate such that when the web exits the oven, the solvent is evaporated to a level that is acceptable for the topical application of the transdermal system. For example, the temperature in the oven may range from 40° C. to 250° C., preferably from 60° C. to 100° C. The acceptable range of residual solvent concentrations is from 0 to 5000 ppm, preferably 0 to 100 ppm. At the oven exit, the adhesive is covered by a backing film. The acceptable range of thickness for the dried adhesive/fentanyl/plasticizer layer alone is 12.5 to 250 μ, preferably 25-125 μ. The multilayered composition is rolled onto a core after application of the backing film and stored for subsequent processing.

Optionally, additional layers can be adjoined to this composition. One common set of layers that can be added is a rate-controlling membrane and an additional adhesive layer. This can be performed in the following manner:

E. An adhesive/plasticizer solution is prepared as in step A above, without fentanyl.

F. The adhesive/plasticizer solution is cast in the same manner as the mixture described in step D above, with the exception that the adhesive is covered with a rate-controlling membrane rather than a backing film.

G. The composition prepared in step D is adjoined to the composition prepared in step F by unrolling the two multi-laminate films from their respective cores, stripping the protective liner from the composition prepared in step D as the film is unrolled, laminating the exposed fentanyl/adhesive/plasticizer layer to the exposed surface of the rate-controlling membrane of the composition prepared in Step F, and rolling this combined multilaminate composition onto a core for subsequent processing. Pressure may be applied during this process to join the adhesive surface to the membrane surface.

Subsequent to production of the multilaminate compositions from either step D or step G, the final transdermal systems can be prepared in the following manner:

H. The multilaminate film, from either step D or step G, is unrolled and passed through a diecutting machine which punches the film into a transdermal system of the proper size and shape. The size of the punched system may range from an area of 1 cm² to 200 cm², preferably 3 cm² to 50 cm². The punched system may be any suitable shape, including but not limited to square, rectangular, triangular, round, or oval, including variations thereof. The system may be punched so that all layers are the same size and shape, or some layers may be different. In order to facilitate the removal of the protective liner before use of the system, the protective liner may have different size or shape. For example, the protective liner may be slightly larger that the remainder of the system (oversized liner), or the liner may have an extension outside the remainder of the system at one or more corners (peel tab). Additionally, the remainder of the system may have an extension (peel tab) at one or more corners. In addition, the liner may have easy-opening score marks or lines.

I. The system punched in step H is enclosed in a suitable primary container which protects it from the external environment. This primary container typically consists of two identical sections of packaging film joined together at the peripheral edges with the system contained inside. The packaging film consists of a heat-sealable layer adjacent to a barrier layer and any suitable layers attached to the barrier layer. The two identical sections of the packaging film are configured so that their heat-sealable layers are touching with the system between the two films. Heat and pressure are applied to the peripheral edges so that the system is sealed within, but not damaged by the applied heat. The heat-sealable layer consists of a polymer which becomes molten when heat is applied. Typical polymers used in this application include, but are not limited to, polyethylene, Barex, polyethylene-(vinyl acetate) copolymer, and ionomer resin (Surlyn®). The barrier layer in the packaging film typically is aluminum at a thickness of 0.00035 to 0.0007 inch. Many different materials may be placed outside the barrier layer, such as polymer films or paper films.

It is recognized that those skilled in the art may conduct this process in many different ways to yield the same result. For example, steps in the mixing or coating processes might be conducted in different order or by different means.

In another aspect, the present invention also includes methods of treating acute and chronic pain, and/or inducing and maintaining analgesia. In preferred embodiments, the invention provides methods of inducing and maintaining analgesia by placing a fentanyl containing medical device in percutaneous drug flow permitting contact with an area of mammalian skin, preferrably human skin. A fentanyl-containing device in accordance with this invention may be used to treat any condition capable of treatment with fentanyl, e.g., chronic and acute pain. The device can be placed on the skin and allowed to remain for an administration period sufficient to achieve or maintain the intended therapeutic effect. The time that constitutes a sufficient administration period can be selected by those skilled in the art with consideration of the flux rate of the device of the invention and of the condition being treated. In preferred embodiments, the medical devices of the present invention are maintained in drug flow permitting contact with an area of mammalian skin for a medically appropriate administration period.

Transdermal delivery of drugs offers a means of circumventing the problems of overdosing and underdosing that are associated with conventional drug delivery methods. When a drug is administered intravenously or orally, the initial level of drug in the blood rapidly rises to a maximum, which is generally much higher than the therapeutically effective level of the drug. After the maximum level in the blood is reached, the concentration then falls slowly as the drug is distributed, metabolized, excreted, or degraded. Eventually, the blood concentration of the drug falls below the therapeutically effective level (i.e., there is "underdosing"). At this point, the drug needs to be re-administered to achieve effectiveness. Maintaining the blood concentration of drug between the minimum therapeutically effective level and toxic levels is important. One way to achieve this is to administer lower drug doses to the patient more frequently. This, however, is an unacceptable alternative in most instances, due to problems with patient compliance. The transdermal delivery of drugs can be designed so that the rate of delivery of the drug closely follows the rate of the clearance of the drug from the environment, thus keeping constant levels of drug in the blood, and reducing drug waste and overdosing problems.

In addition to the advantage of being able to control drug delivery rates, transdermal drug delivery also provides a comfortable, convenient and non-invasive method of administering drugs. Gastrointestinal irritation and other side-effects associated with oral drug delivery may be reduced or eliminated, and patient anxiety regarding invasive delivery methods, such as needles, is also eliminated.

EXAMPLES

The preferred embodiments of the present invention will now be further described through the following examples set forth herein below which are intended to be illustrative of the preferred embodiments of the present invention and are not intended to limit the scope of the invention as set forth in the appended claims.

Example 1

Measuring in Vitro Fentanyl Permeation Rates

The permeation data are obtained using the following test method. A permeation cell manufactured by Permegear is used. The permeation cell is made of two parts, a cell insert and a cell bottom. The human cadaver skin is placed inside the cell bottom with the stratum corneum side facing up. The solid drug form is then placed on the cadaver skin, after removing the strippable release liner, with the exposed adhesive layer contacting the surface of the stratum corneum. The cell insert is placed on top of the skin and clamped in using a hook latch system. The appropriate receptor medium is pushed through a network of tubing. The flowrate of the receptor medium is controlled by a peristaltic pump. The receptor medium typically consists of phosphate buffered saline or normal saline solution. The receptor medium pumped through the tubing passes underneath the skin inside the cell bottom, and the medium is collected in a vial over preset time intervals. The cell, skin, drug form, and receptor medium are all heated to 32° C.±1.5° C. by an attached waterbath. The concentration of the drug in the receptor medium collected from each time period is measured using HPLC, or some other suitable analytical technique. The permeation rate or flux over each time period, defined as the rate of drug transport across the skin per unit area of skin, is calculated from the measured concentration, the volume of receptor solution collected, the duration of the time period, and the known area of the transport region in the permeation cell.

Example 2

Preparing a Multilayer Medical Device for Transdermal Administration of Fentanyl Transdermal therapeutic systems according to FIG. 1 utilizing a polymeric drug reservoir were prepared in 6-inch by 8-inch laminates. An amount of fentanyl base sufficient to comprise 5% of the formulation in the dry basis was added to isopropanol ("IPA") and stirred to disperse the drug. Medical Fluid 360 (Dow Corning) ("Medical Fluid") was added to the isopropanol-fentanyl dispersion in amounts sufficient to generate a mixture containing 150 mg/g of fentanyl in a 64% solvent solution. Seventy percent amine resistant silicone in heptane was added to this mixture slowly with stirring and mixed until a one layer clear solution was formed (approximately thirty minutes). This clear solution containing drug, Medical Fluid, and IPA was solvent coated onto a treated release liner to form what will be the drug reservoir layer for the system. After evaporation of the solvent, the exposed adhesive was then covered with a backing. The backing layer was comprised of a multilaminate of polyethylene terephthalate and EVA. In a separate process a 2 mil thick skin contact adhesive layer was cast onto a fluorocarbon-diacrylate treated polyester film which comprised the release liner for the system. The contact layer was comprised of an amine resistant silicone medical adhesive plasticized with Medical Fluid. A 4 mil thick rate controlling membrane comprised of EVA (19% VA) was pressure laminated to the exposed side of the contact adhesive. The release liner was then removed from the drug containing layer, and it was laminated to the rate controlling membrane on the skin contacting adhesive layer. This process resulted in a five layer system combined from the bottom to top as follows: release liner, skin contacting adhesive layer, rate controlling membrane, drug reservoir layer, backing layer as depicted in FIG. 1. The laminates were allowed to equilibrate for at least 7 days in order to reach equilibrium concentration of the drug in the rate controlling and adhesive layers. After this time the skin contacting adhesive layer contained an amount of drug and the drug concentration in the reservoir was reduced slightly.

Figure 8:
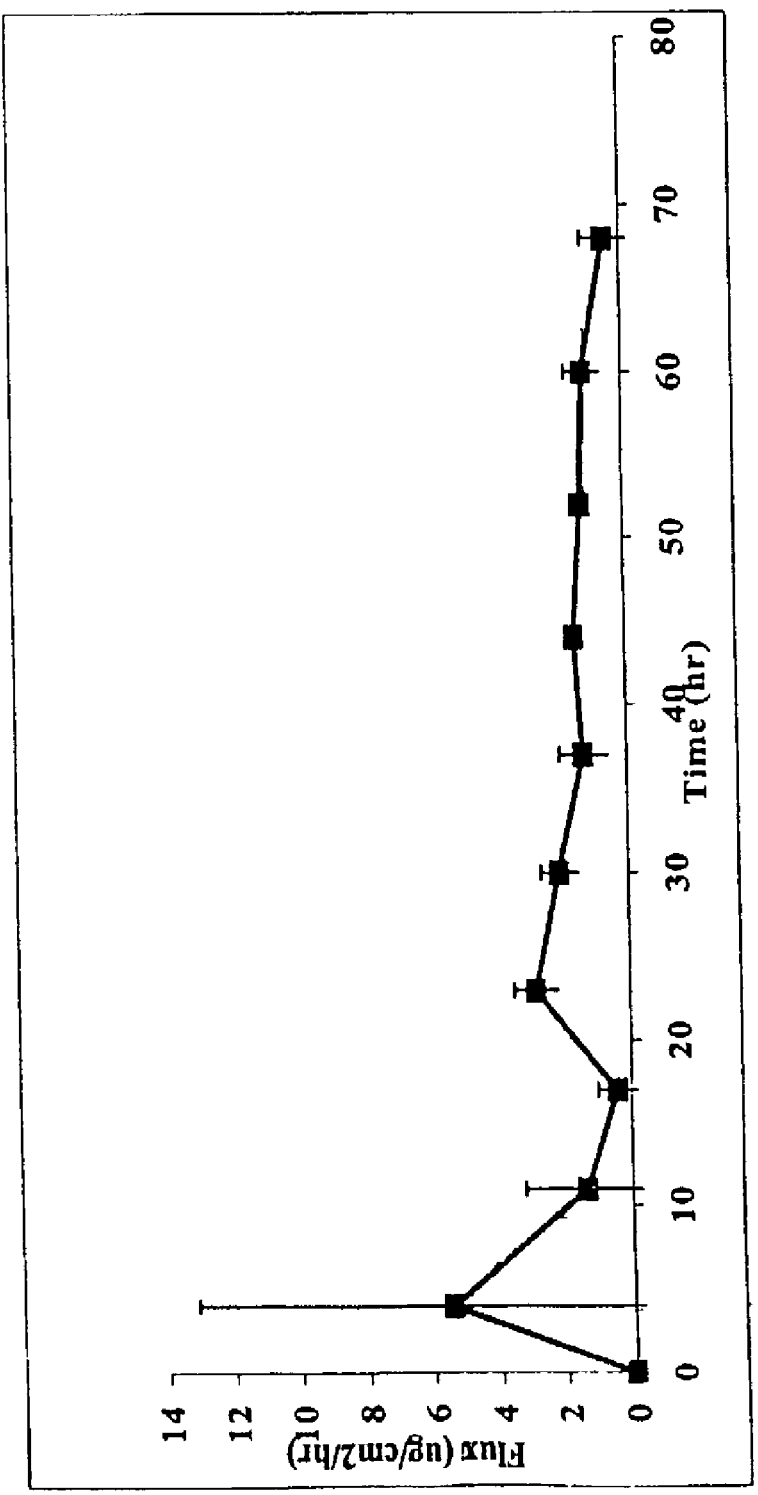
FIG. 8 is a graph of the permeation profile of fentanyl from a transdermal medical device comprising a polydimethylsiloxane matrix material and a fentanyl flux rate lowering effective polydimethylsiloxane emulsion plasticizer loading.

The in vitro fentanyl flux through cadaver skin into an infinite aqueous sink at 32° C. was measured and is shown as FIG. 8. FIG. 8 provides a graphical representation of the rate of flux of fentanyl, in $\mu g/cm^2$ as a function of time in hours, from a transdermal medical device comprising a polydimethylsiloxane matrix material and a fentanyl flux rate lowering effective polydimethylsiloxane emulsion plasticizer loading. The graph shows fentanyl flux rates as a function of time, as measured through cadaver skin in vitro at 32 deg. C. As can be seen the fentanyl flux increased to a peak of approximately 5.43 $\mu g/cm^2/hr$ in slightly more than four hours. Absorption of the drug in skin occurred during the time the drug flux was increasing to its steady value. The graph in FIG. 8 was prepared from data obtained through tests of a transdermal medical device of Example 2, comprising a fentanyl flux rate lowering effective plasticizer loading.

Example 3

Large Scale Preparation of a Fentanyl Flux Rate Lowering Composition

Systems similar to those described in Example 2 were fabricated except that the solutions were mixed in large batches in a pilot plant according to the following instructions. The compositions were used to make transdermal therapeutic systems according to FIG. 1 utilizing a polymeric drug reservoir were prepared in 6-inch by 8-inch laminates. One to eighteen liters of silicone adhesive were mixed using either an electric or pneumatically driven mixing unit. In a separate vessel isopropyl alcohol was added to fentanyl and mixed to form a slurry. The isopropyl alcohol ("IPA") in this process was used to disperse the drug and facilitate the mixing process. After the fentanyl IPA slurry was sufficiently mixed, it was then added to silicone adhesive in heptane. Silicone Medical Fluid plasticizer (Medical Fluid 360 from Dow Corning) was then added and the entire mixture of silicone adhesive matrix material, Medical Fluid plasticizer, fentanyl, and IPA was allowed to mix for several hours. Experimental solutions were mixed and sampled at top, middle and bottom for content uniformity. Uniformity was normally achieved after two hours.

In a separate vessel, a contact adhesive layer solution was formed by adding one to eighteen liters of silicone adhesive matrix material to a mixer having either an electric or pneumatically driven mixing unit. A sufficient amount of Medical fluid plasticizer was added to form a 5% plasticizer concentration in the dry basis. The solution was mixed to form a one layer clear solution.

A Kraemer Coating machine was used to lay down the adhesive/solvent/drug mixture on a liner (such as polyester), evaporate the solvent, and laminate another substrate (backing film) to it. The adhesive contact layer was produced in a similar fashion except a 4 mil rate controlling membrane was laminated to the upper side after the contact adhesive solution is cast on the liner. The release liner was removed from the drug reservoir and the drug reservoir was then laminated to the rate controlling membrane. This multilaminate depicted in FIG. 1 was punched and pouched to make complete transdermal delivery systems.

Example 3a

Comparative Example Showing Large Scale Preparation of Drug Containing Fentanyl Flux Rate Lowering Composition without Alcohol Dispersing Agent A drug reservoir was prepared using equipment similar to those described in Example 3 except that no isopropyl alcohol (IPA) was used in the mixing process. The fentanyl was added directly to the silicone adhesive in heptane. The absence of IPA in the mixing process resulted in the uneven dispersion of the fentanyl within the mixture. The fentanyl settled down to the bottom of the mixing vessel 5-12 hours after mixing was terminated. The settling of the drug makes achieving uniformity nearly impossible.

Example 3b

Comparative Example Showing Laboratory Scale Preparation of Drug Containing Fentanyl Composition without Alcohol Dispersing Agent and with Less than a Flux Rate Lowering Effective Amount of Plasticizer Systems similar to Example 2 were fabricated with the exception that no plasticizer and no IPA were used in the mixing process. In a lab scale formulation it was possible to achieve some form of uniform dispersion through sonication and vigorous mixing without using IPA to facilitate dispersion. However, during coating a large percentage of the fentanyl crystals are too large to be coated in the laminate. For these systems the target drug loading was 225 mcg/cm$^2$ and the control membrane was a 4 mil EVA film (19% VA). The in vitro transport rate through skin is shown in FIG. 3.

Example 4a

Preparation of and Fentanyl Flux from a Multilayer Medical Device for Transdermal Administration of Fentanyl with a Flux Rate Lowering Effective Amount of Plasticizer Systems similar to those described in Example 2 were manufactured with a 5% w/w plasticizer content and the in vitro fentanyl flux rate through cadaver skin into an infinite aqueous sink at 32° C. was measured and is shown in FIG. 5 (curve 540) for a first system and in FIG. 6 (curve 640) for a second system, and in the curve in FIG. 8 for a third system.

Example 4b

Preparation of and Fentanyl Flux from a Multilayer Medical Device for Transdermal Administration of Fentanyl with a Flux Rate Lowering Effective Amount of Plasticizer Systems similar to those described in Example 2 are manufactured except that the drug reservoir contains 6% medical fluid. As a result of the increase in the amount of plasticizer content the resulting flux through skin is lower when compared to the normal input of 5% w/w plasticizer content. This results in a lower initial burst in drug delivery than in systems containing 5% fluid. The comparison of in vitro fentanyl flux from formulations containing 5% and 6% medical fluid through cadaver skin into an infinite aqueous sink at 32° C. was measured, is shown in FIG. 6 and discussed above.

Example 4c

Preparation of and Fentanyl Flux from a Multilayer Medical Device for Transdermal Administration of Fentanyl with a Flux Rate Lowering Effective Amount of Plasticizer Systems similar to those described in Example 5 are manufactured except that the drug reservoir contains 7% medical fluid. As a result of the increase in the amount of plasticizer content the resulting flux through skin is higher when compared to the normal input of 5% w/w plasticizer content. This results in a higher initial burst in drug delivery than in systems containing 5% fluid. The comparison of in vitro fentanyl flux from formulations containing 5% and 7% medical fluid through cadaver skin into an infinite aqueous sink at 32° C. was measured, is shown in FIG. 6 and discussed above.

Comparative Example 5a

Preparation of and Fentanyl Flux from a Multilayer Medical Device for Transdermal Administration of Fentanyl with Less than a Flux Rate Lowering Effective Amount of Plasticizer Systems similar to those described in Example 2 were manufactured except that the drug reservoir contained no medical fluid. As a result of the absence of plasticizer content the resulting flux through skin increased nearly one and a half times when compared to the normal input of 5% w/w plasticizer content. This resulted in a higher initial burst in drug delivery than in systems containing 5% fluid. The comparison of in vitro fentanyl flux from formulations containing 5% and 0% medical fluid through cadaver skin into an infinite aqueous sink at 32° C. was measured and is shown in FIG. 5.

Comparative Example 6a

Preparation of and Fentanyl Flux from a Multilayer Medical Device for Transdermal Administration of Fentanyl with Greater than a Flux Rate Lowering Effective Amount of Plasticizer Systems similar to those described in Example 2 were manufactured except that the drug reservoir contained 20% medical fluid by weight. As a result of the high plasticizer content the resulting flux through skin nearly tripled when compared to the normal input of 5% w/w plasticizer content. This is illustrated by FIG. 4.

Comparative Example 6b

Preparation of and Fentanyl Flux from a Multilayer Medical Device for Transdermal Administration of Fentanyl with Various Amounts of a Flux Rate Lowering Effective Amount of Plasticizer Systems similar to those described in Example 2 were manufactured except that the drug reservoir contained 7% medical fluid by weight. As a result of the high plasticizer content the resulting flux through skin nearly tripled when compared to the normal input of 5% w/w plasticizer content. This is illustrated by FIG. 6.

Comparative Example 7

Figure 7A:
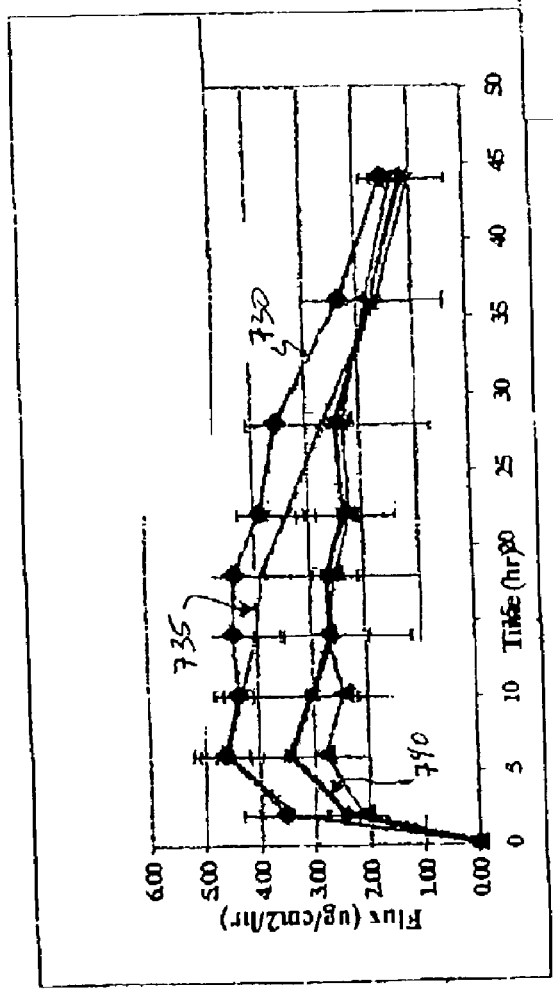
FIGS. 7A & B displays several graphs comparing the permeation profiles showing fentanyl flux rates from transdermal medical devices, with similar profiles derived from a commercially available liquid drug reservoir fentanyl transdermal patch.
Figure 7B:
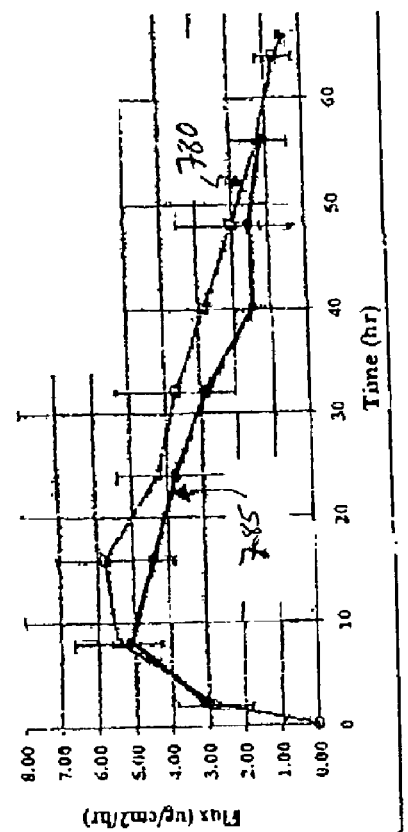

Preparation of and Fentanyl Flux from a Multilayer Medical Device for Transdermal Administration of Fentanyl with a Commercially Available Fentanyl Patch FIGS. 7A & 7B compare the permeation profiles showing fentanyl flux rates from transdermal medical devices, with similar profiles derived from a commercially available liquid drug reservoir fentanyl transdermal patch. FIGS. 7A & 7B show fentanyl flux rates in µg/cm$^2$ as a function of time in hours, as measured through cadaver skin in vitro at 32 deg. C.

FIG. 7A compares the permeation profiles showing the fentanyl flux rate from a first sample, curve 730, and a second sample, curve 740, with the fentanyl flux rate derived from a transdermal medical device of Example 2 comprising a fentanyl flux rate lowering effective plasticizer loading, curve 735. Both the first sample and the second sample were commercially-available DURAGESIC® fentanyl transdermal medical device.

Similarly, FIG. 7B compares the fentanyl flux rate from a third sample from a commercially available DURAGESIC® fentanyl transdermal medical device, curve 780, with the fentanyl flux rate derived from a transdermal medical device made according to Example 2 comprising a fentanyl flux rate lowering effective plasticizer loading, curve 785.

The present invention having been disclosed in connection with the foregoing embodiments, additional embodiments will now be apparent to persons skilled in the art. The present invention is not intended to be limited to the embodiments specifically mentioned, and accordingly reference should be made to the appended claims rather than the foregoing discussion, to assess the spirit and scope of the present invention in which exclusive rights are claimed.

We claim:
1. A medical device for transdermal administration of a drug through an area of human skin during an administration period, the medical device comprising:
 a) a solid drug reservoir layer having a top side and a bottom side and an external edge, wherein the solid drag reservoir layer is a composition consisting essentially of:
  i) an amine-resistant polydimethylsiloxane adhesive matrix having a molecular weight of between 100,000 and 5,000,000;
  ii) a drug selected from the group consisting of fentanyl and sufentanyl; and
  iii) a drug flux rate-lowering amount of between 4 and 7% w/w of dimethicone having a viscosity of 20 to 12,500 centistoke mixed with the adhesive matrix;
 b) a rate controlling membrane having a top and a bottom side, wherein the top side of the rate controlling membrane is contiguously disposed with respect to the bottom side of the drug reservoir layer;
 c) an adhesive layer having a top and a bottom side, wherein
  i) the top side of the adhesive layer is contiguously disposed with respect to the bottom side of the rate controlling membrane;
  ii) the adhesive layer is adapted to be maintained in drug-transferring relationship to the human skin;
  iii) the adhesive layer comprises an amine-resistant polydimethylsiloxane adhesive matrix having a molecular weight of between 100,000 and 5,000,000; and
  iv) a drug flux rate-lowering amount of between 4 and 7% w/w of the adhesive composition of dimethicone having a viscosity of 20 to 12,500 centistoke mixed with the adhesive matrix, and
 wherein the drug reservoir layer comprises at least about 1% w/w drug.
2. The medical device of claim 1, wherein the drag reservoir layer comprises no more than about 15% w/w drug.
3. The medical device of claim 2, wherein the drug reservoir layer comprises, no more than about 6% w/w drug.
4. The medical device of claim 1, wherein the drug reservoir layer comprises at least about 1 mg of drug.
5. The medical device of claim 1, further comprising:
 a backing layer having a top side and a bottom side, wherein the bottom side of the backing layer is contiguously disposed to the top side of the solid drug reservoir layer; and
 the backing layer does not completely seal the external edge of the solid drug reservoir layer.
6. The medical device of claim 1, wherein the composition in said solid drug reservoir layer comprises no less, than 5% w/w and no more than 6% w/w of dimethicone.
7. The medical device claim 6, wherein the composition in said solid drug reservoir layer comprises about 5% w/w dimethicone.
8. The medical device of any one of claims 6-7, wherein the dimethicone has a viscosity of 300 to 400 centistoke.
9. The medical device of claim 8, wherein the dimethicone is silicone fluid.
10. The medical device of any one of claims 6-7, wherein the amine-resistant polydimethylsiloxane adhesive matrix in said solid drug reservoir layer has a molecular weight of between 500,000 and 1,500,000.

11. The medical device of claim 1, wherein the drug is fentanyl.

12. The medical device of claim 1, wherein the composition in said solid drug reservoir layer comprises at least about 4% w/w drug.

13. The medical device of claim 1, wherein the composition in said solid drag reservoir layer comprises no more than about 6% w/w drug.

14. The medical device of claim 12, wherein the composition in said solid drug reservoir layer comprises no more than about 6% w/w drug.

15. The medical device of claim 1, wherein the composition in said solid drug reservoir layer comprises at least about. 1 mg of drug.

16. The medical device of claim 15, wherein the composition in said solid drug reservoir layer comprises no more than about 30 mg of drug.

17. The medical device of claim 1, wherein the rate controlling membrane comprises:
   a polyethylene-(vinyl acetate) copolymer with up to 33% vinyl acetate, the polyethylene-(vinyl acetate) copolymer having a molecular weight of 10,000 or greater, wherein the thickness and vinyl acetate content of the rate controlling membrane are selected to provide a 0.5 to 10 μm/cm²hr permeation rate through the rate controlling membrane at 32° C.

18. The medical device of claim 17, wherein the rate controlling membrane comprises polyethylene-(vinyl acetate) copolymer with 19% w/w vinyl acetate.

19. The medical device of claim 1, wherein the molecular weight of the amine-resistant polydimethylsiloxane adhesive matrix, the viscosity of the dimethicone, and the weight percentage of dimeihicone in the adhesive layer are the same, respectively, as in the drug reservoir layer.

20. The medical device of claim 19, wherein dimethicone is present in the drug reservoir and adhesive layers at 5-6% w/w.

21. The medical device of claim 1, further comprising:
   a strippable release liner having a top and a bottom side,
   wherein the top side of the strippable release liner is contiguously disposed to the bottom side of the adhesive layer.

* * * * *